(12) United States Patent
Hansson

(10) Patent No.: US 8,764,444 B2
(45) Date of Patent: Jul. 1, 2014

(54) DENTAL FIXTURE

(75) Inventor: Stig Hansson, Askim (SE)

(73) Assignee: Dentsply International Inc., York, PA (US)

( * ) Notice: Subject to any disclaimer, the term of this patent is extended or adjusted under 35 U.S.C. 154(b) by 0 days.

(21) Appl. No.: 13/067,433

(22) Filed: Jun. 1, 2011

(65) Prior Publication Data

US 2011/0306016 A1 Dec. 15, 2011

Related U.S. Application Data

(60) Provisional application No. 61/344,207, filed on Jun. 10, 2010.

(30) Foreign Application Priority Data

Jun. 10, 2010 (EP) ..................................... 10165555

(51) Int. Cl.
*A61C 8/00* (2006.01)

(52) U.S. Cl.
USPC .......................................... 433/173; 433/174

(58) Field of Classification Search
CPC ................. A61C 8/00; A61C 8/0012–8/0013; A61C 8/0022–8/0025; A61C 2008/0046
USPC ....................................... 433/172–176, 201.1
See application file for complete search history.

(56) References Cited

U.S. PATENT DOCUMENTS

| 5,645,740 | A | 7/1997 | Naiman et al. |
| 6,419,491 | B1 | 7/2002 | Ricci et al. |
| 2005/0234558 | A1 | 10/2005 | Petersson et al. |
| 2008/0044795 | A1 | 2/2008 | Hall |
| 2008/0261178 | A1 | 10/2008 | Homann et al. |
| 2009/0258327 | A1 * | 10/2009 | Zipprich ........................ 433/173 |
| 2010/0173264 | A1 | 7/2010 | Fredriksson et al. |

FOREIGN PATENT DOCUMENTS

| EP | 1982670 A1 | 10/2008 |
| EP | 2022447 A1 | 2/2009 |
| WO | WO-2005055858 A1 | 6/2005 |
| WO | WO-2007091155 A1 | 8/2007 |

OTHER PUBLICATIONS

P.Tschantz, et al., "La Surcharge mécanique de l'os vivant" Annales d'Anatomie pathologique, Paris, tome 12, n° 3, pp. 223-248, 1967, with English language summary on p. 247.
J. Robert Kelly, "Ceramics in Restorative and Prosthetic Dentistry," Annu. Rev. Mater. Sci. 1997. Pages 443-68.
H. M. Frost, "A Brief Review for Orthopedic Surgeons: Fatigue Damage (Microdamage) in Bone (its Determinants and Clinical Implications," Journal of Orthopaedic Science. 1998, pp. 272-281.

(Continued)

*Primary Examiner* — Cris L Rodriguez
*Assistant Examiner* — Edward Moran
(74) *Attorney, Agent, or Firm* — David A. Zdurne; Douglas J. Hura; Leana Levin

(57) ABSTRACT

The invention relates to a dental fixture for insertion into a human jawbone. The fixture comprises a bone-contacting surface, wherein a resulting filtered set of data presents a surface roughness having the roughness average parameter $S_a \geq 1$ μm and the two-dimensional mean slope parameter $R_{s i} \geq \tan 30°$ for at least 15% of the bone-contacting surface.

18 Claims, 7 Drawing Sheets

(56) References Cited

OTHER PUBLICATIONS

D.B. Burr, et al., "Bone Remodeling in Response to In Vivo Fatigue Microdamage," J. Biomechanics vol. 18, No. 3, 1985. pp. 189-200.

P. Zioupos, et al., "Fatigue Strength of Human Cortical Bone: Age, Physical, and Material Heterogeneity Effects," Journal of Biomedical Materials Research Part A, 2008, pp. 627-636.

R. Haas, et al., Survival of 1,920 IMZ Implants Followed for up to 100 MonthsInternational Journal of Oral Maxillofacial Implants, 1996. pp. 581-588.

International Search Report dated Sep. 23, 2011 issued in corresponding International Application No. PCT/EP2011/059035.

Written Opinion dated Sep. 23, 2011 issued in corresponding International Application No. PCT/EP2011/059035.

European Search Report dated Nov. 19, 2010.

* cited by examiner

DENTAL FIXTURE

CROSS-REFERENCE TO RELATED APPLICATIONS

This application claims priority under 35 U.S.C. §119 to U.S. Application No. 61/344,207, filed Jun. 10, 2010, and further claims priority under 35 U.S.C. §119 to European Patent Application No. 10165555.3, filed Jun. 10, 2010, in the European Patent Office, the entire contents of each of which are hereby incorporated by reference.

TECHNICAL FIELD

The present invention relates to a dental fixture for insertion into a human jawbone.

BACKGROUND

A frequent way today to restore a damaged limb, such as lost tooth, is to install a fixture in the adjacent bone tissue and replace the damaged parts. In this respect, for a successful result, the fixture should become fully stable and correctly joined to the bone. The term osseointegration is used for this joining effect, the basic meaning of this term being the bone tissue growth into the fixture surface. The two major contributors to this joint are a mechanical joint and an organic joint. The former being generally influenced by the macro geometry of the bore into which the fixture is installed, and by the macro geometry of the fixture, and is a direct effect of how well these two work together. The latter one being a continuously evolving and developing effect, particularly the time immediately after installation, and being generally influenced by how well the micro surface structure of the fixture interacts with the bone tissue.

Due to ingrowth there will be an interlocking effect between the bone and the fixture. Also, the mechanical joint is developed over time since the bone tissue, under ideal conditions, may grow into surface cavities of the fixture, and grow into voids left between the fixture and the bore after installation.

Interaction of mechanical and organic aspects will affect the bone ingrowth and joint between the bone and the projecting surface structure of the fixture. The projecting surface structure may be in the form of threads, annular ridges, lines or patterns of beads etc. Further a blasted, or otherwise roughened, surface of the fixture will provide advantageous conditions for this process.

Dental fixtures are subjected to functional forces. These forces are transmitted to the surrounding bone as compressive forces, tensile forces and shear forces at the fixture/bone interface. The higher the ability of the interface to withstand these three types of forces the bigger the loads the fixture can support. The ability of the interface to resist compressive forces is relatively large. In comparison, the ability of the interface to stand tensile forces is insignificant or low. As regards the third force, research has been spent on trying to enhance the fixture/bone interface shear strength through modification of the micrometer (μm)-sized roughness of the fixture surface.

The roughness of the fixture surface may be regarded as comprising pits and protrusions. Bone is allowed to grow into the pits on the fixture surface and create retention. The bone which has grown into the pits may be referred to as bone plugs. Correspondingly, protrusions will engage the bone and create retention.

It has been found that despite the effort of providing increased retention by means of micro-roughening the fixture surface, the resulting bone plugs and the bone portions engaged by fixture protrusions are often broken in use, whereby the intended functionality of the roughness is at least partly lost.

An object of the invention is therefore to provide a fixture which enables formation of bone that create long term retention, particularly in cortical bone tissue. These and other objects, which will become apparent in the following, are accomplished by the invention as defined in the accompanying claims.

SUMMARY OF THE INVENTION

The present invention is i.a. based on an insight that for bone plugs which protrude into pits of roughness of the fixture surface, the failure mechanism will either be shear fracture or compressive fracture of the bone plugs depending on the relationship between the bone shear strength and bone compressive strength and on the geometry of the pits.

The inventor of the present patent application has realised that the relationship between bone shear strength and bone compressive strength may be calculated under the following assumptions: A pit of a fixture roughness is schematically illustrated in the accompanying FIG. 2. Assuming a width of $\Delta y$ for the illustrated pit, shear fracture occurs when the shear force $F_{sh}$ reaches $F_{sh}=T_{bf}2\Delta x \, \Delta y$ (shear strength of bone $T_{bf}$ multiplied by fracture surface area). Compressive fracture occurs when the compressive force $F_c$ reaches $F_c=\sigma_{bcf}\Delta x \, \Delta y/\cos(\alpha)$, wherein $\sigma_{bcf}$ is the compressive strength of bone. Then the horizontal component $F_{c//}=\sigma_{bcf}\Delta x \, \Delta y \cdot \tan(\alpha)$. This implies that if $T_{bf}2\Delta x \, \Delta y < \sigma_{bcf}\Delta x \, \Delta y \cdot \tan(\alpha)$ failure occurs through shear. An alternative expression of this condition is that if $$T_{bf}/\sigma_{bcf} < \tan(\alpha)/2$$

failure occurs through shear. If this condition is not fulfilled failure occurs through compression.

Microcracks, probably caused by fatigue, are normally present in haversian bone (Tschantz et al. *Ann Anat Path* 1967; 12:223-248). The number of chewing cycles per day is in the range of 800-1400 (Kelly. *Ann Rev Mater Sci* 1997; 27:443-468). Thus, on average, the number of chewing cycles per day is 1100. Assuming the 80/20-rule: 20% of the loads/chewing cycles create 80% of the microdamages, means that about 20% of 1100, i.e. 220 chewing cycles per day create the majority of the microdamages.

It takes at least 3 months to repair microdamaged bone (Frost. *J Orthop Sci* 1998; 3:272-281). If the rate of microdamage production exceeds the healing rate bone loss results (Burr et al. *J Biomech* 1985; 18:189-200). Thus, at steady state, the majority of the microdamage production over said 3 months (about 90 days) of repair is 220*90 chewing cycles=19800 chewing cycles. In Zioupos et al. *J Biomed Mater Res* 2008; 86A:627-636 a diagram shows the relationship between shear strength and compressive strength for cortical bone as a function of the number of load cycles. For 19800 cycles this relationship is about 0.29. Inserting this shear relationship of the strength and compressive strength in the above expression results in:

$$0.29 < \tan(\alpha)/2$$

which approximately results in $\alpha > 30°$.

This should mean that the shift between compressive and shear fracture occurs approximately when the angle $\alpha = 30°$. Thus, the inventor has realized that by providing the fixture with a roughness in which the pit wall is inclined at 30° or more in relation to the surrounding surface, the shear strength of the fixture/bone interface is increased. From a practical point of view, rather than providing each and every individual pit wall with said angle, at least the mean slope ($R_{sl}$) of the surface roughness should correspond to the desired inclination. The component of $F_c$ directed perpendicularly to the fixture surface will create a gap between fixture and bone, which will reduce the shear strength of the fixture/bone interface. The larger the mean slope, the smaller are these $F_c$ components directed perpendicularly to the fixture surface, which means a smaller gap between fixture and bone and a smaller reduction of the shear strength of the fixture/bone interface. In other words, the higher the mean slope, the lower the outwardly directed pressure against the bone tissue, and thereby better strength of the fixture/bone interface. Mean slope $R_{sl}$ is defined as $$R_{sl} = \frac{1}{m-1} \sum_{i=1}^{m-1} \left| \frac{z_{i+1} - z_i}{x_{i+1} - x_i} \right|$$

wherein
 m is the number of measuring points,
 the numerator is the difference in height between two consecutive measuring points relative a base line, and
 the denominator is the distance between said two consecutive measuring points along the base line.

When analyzing small surface topographies in the micrometer region, it is appropriate to use magnifying equipment. The inventor has identified a 50× objective as adequate for characterizing a suitable surface roughness. In addition, white light interferometry is a suitable procedure for scanning the surface.

The inventor has also realized that, due to the formation of a gap between fixture and bone mentioned above, in order to obtain the desired interlocking effect, the bone plugs should have a certain size and, therefore, the angle of the walls of pits of smaller size is of less relevance. Thus, this kind of "noise" should be filtered, so that only relevant roughness sizes are taken into account. A Gaussian 3 µm low-pass filter has been found appropriate when analyzing the surface roughness of the fixture for micro-pit walls with at least 30° inclination. Similarly, it is only the roughness at the micrometer-level which is of interest, and not the waviness or other larger variations such as thread profiles. Therefore, use of a Gaussian 50 µm high-pass filter has been found appropriate when analyzing said surface roughness.

Due to the formation of a gap between the fixture surface and the bone when the fixture/bone interface is exposed to shear force the average distance from the surface of the roughness to an average plane must not be too low, because if the above-mentioned gaps are large, there is a risk of bone plugs not being in adequate interlocking contact with the fixture. The inventor has found that the roughness average parameter $S_a$ should be ≥1 µm. The roughness average $S_a$ is defined as:

$$S_a = \frac{1}{MN} \sum_{k=0}^{M-1} \sum_{l=0}^{N-1} |z(x_k, y_l)|$$

In summary, the invention is based on the insight that by providing a surface roughness with relatively large mean slope parameter $R_{sl}$ and relatively large roughness average parameter $S_a$ the shear strength may be increased without risking reduced fixture/bone contact.

According to at least one aspect of the invention, a dental fixture for insertion into a human jawbone, comprising a bone-contacting surface, wherein a at least 15% of the bone-contacting surface is designed such that when a Gaussian 50 µm high-pass filter and a Gaussian 3 µm low-pass filter is applied to an original unfiltered set of measurement data which represents a topography of said surface and which is obtained at 50 times magnification by white light interferometry, the resulting filtered set of data presents a surface roughness having the roughness average parameter $S_a \geq 1$ µm and the two-dimensional mean slope parameter $R_{sl} \geq \tan 30°$.

A dental fixture is for use as the anchoring member of a dental prosthesis. The dental prosthesis may be connected to the fixture via a superstructure, such as an abutment, which extends through the gingiva. Alternatively, the dental prosthesis may be attached directly to the fixture. The structure supporting the prosthesis, whether it is only a fixture or the combination of fixture and superstructure, may be referred to as an "implant". A fixture may have both bone-contacting surface (i.e. surface that is intended to, at least after osseointegration, be in contact with bone tissue) and a gingiva-contacting surface (i.e. intended to be located outside the bone and in contact with the gingiva). The axial length of the bone contacting surface of a fixture may typically be 5-20 mm.

Although the above-defined surface roughness may be present on the entire bone-contacting surface of the fixture, the inventor has realized that an advantageous effect is obtainable with as little as 15% of the bone-contacting surface being provided with the above-defined surface roughness. The above-defined surface roughness is advantageous both in connection with cortical bone and with cancellous bone, thus, the invention is not limited to a specific area. Nevertheless, since the cortical bone tissue is not as flexible as cancellous bone tissue, it may be desirable to at least reduce the risk of breaking cortical bone plugs.

Thus, although the advantageous effect of the surface roughness is not limited to a particular part of the bone/fixture interface, it may be suitable to at least provide the surface roughness at an area of the bone-contacting surface which is intended to engage the cortical bone tissue. This is reflected in at least one example embodiment, according to which said bone contacting surface has a coronal end and an apical end, wherein said surface roughness is present at least at an area located closer to the coronal end than to the apical end, suitably at least at an area located within the first third of the total axial extent from the coronal end to the apical end.

While the thickness of the cortical bone tissue varies from person to person, on average, 3 mm is an adequate estimate. Generally, the coronal layer is located just beneath the gingiva. Thus, according to at least one example embodiment, the above-defined surface structure has an axial length of 3 mm or less than 3 mm, starting at or near a coronal end of the bone-contacting surface.

The term "coronal" is here and throughout this application used to indicate a direction towards a head end or trailing end of the dental fixture. For instance, in a situation where an abutment is connected to a dental fixture, the coronal direction of the abutment would be a direction towards the part of the abutment being directed away from the fixture. Conversely, the term "apical" indicates a direction towards an insertion end of the component. Thus, apical and coronal are opposite directions. Furthermore, the term "axial direction" or "axially" is used throughout this application to indicate a direction taken from the coronal end to the apical end, or vice versa.

Although 15% of the bone-contacting surface provides an adequate effect, suitably a larger area or even the entire bone-contacting surface may be provided with the above-defined surface roughness. Thus, according to at least one example embodiment, at least 30%, suitably at least 50%, such as at least 70% of the bone-contacting surface is designed such that when a Gaussian 50 μm high-pass filter and a Gaussian 3 μm low-pass filter is applied to an original unfiltered set of measurement data which represents a topography of said surface and which is obtained at 50 times magnification by white light interferometry, the resulting filtered set of data presents a surface roughness having the roughness average parameter $S_a \geq 1$ μm and the two-dimensional mean slope parameter $R_{sl} \geq \tan 30°$.

The parameter measurements on the fixture may be performed by means of a surface smoothness instrument, such as MicroXAM 100-HR, manufactured by ADE Phase Shift Technology. The instrument provides white light interferometry for 3D and profile measurements. The collected data may, for instance, be evaluated by means of the software MountainsMAP ver-5.0.4.5276, supplied by Digital Surf.

According to at least one example embodiment, when a Gaussian 4 μm low-pass filter is applied instead of said 3 μm low-pass filter, the resulting filtered image presents a surface roughness having the roughness average parameter $S_a \geq 1$ μm and the two-dimensional mean slope parameter $R_{sl} \geq \tan 30°$. This may be advantageous when measuring on larger surface roughness.

For even larger surface roughness, it may be advantageous to apply a 5 μm low-pass filter. Thus, according to at least one example embodiment, when a Gaussian 5 μm low-pass filter is applied instead of said 3 μm low-pass filter, the resulting filtered image presents a surface roughness having the roughness average parameter $S_a \geq 1$ μm and the two-dimensional mean slope parameter $R_{sl} \geq \tan 30°$.

The inventor has found that the higher the value of the mean slope parameter, the lower the force pressing away the bone. Thus, a larger mean slope results in better strength of the bone. Therefore, according to at least one example embodiment, the two-dimensional mean slope parameter $R_{sl} \geq \tan 35°$, suitably $R_{sl} \geq \tan 40°$.

According to at least one example embodiment, the two-dimensional mean slope parameter $R_{sl} \leq \tan 70°$. Currently, from a manufacturing perspective, a mean slope of tan 70° has been found to be an appropriate upper limit.

According to at least one example embodiment, the roughness average parameter $S_a \geq 1.5$ μm, suitably $S_a \geq 2$ μm. These values of the parameter $S_a$ may further reduce the risk of large gap formation.

According to at least one example embodiment, the fixture comprises a thread for inserting the fixture into the jawbone by means of rotation, wherein the thread is provided with said surface roughness. Generally, when looking in the axial direction of an externally threaded fixture, the threading will present alternating peaks and valleys. The surface roughness may be present either on the peaks or in the valleys, or both on the peaks and in the valleys.

According to at least one example embodiment, the thread has a thread profile comprising two flanks and an apex formed by the intersection of said two flanks, wherein both flanks are provided with said surface roughness. As an alternative, the surface roughness may be provided on only one of the flanks, e.g. only on a coronal flank or only on an apical flank.

According to at least one example embodiment, said surface roughness is superposed by a nanostructure which, when a Gaussian 2 μm high-pass filter is applied to said set of measurement data, has a roughness average parameter $S_a \geq 0.1$ μm. This superposed nanostructure promotes bone ingrowth with the fixture.

According to at least one example embodiment, said surface roughness is produced by any one of or any combination of the methods selected from the group consisting of:
  knurling the surface of the fixture,
  etching,
  blasting,
  nanolithography, and
  laser ablation.

According to at least one example embodiment, the fixture surface is at least partly presented by a machined titanium surface. This has been found to be advantageous both from a biological and a mechanical perspective, in contrast to e.g. a surface coated with hydoxylapatite (HA) or a titanium plasma sprayed (TPS) surface. As regards HA coated surfaces, they tend to present relatively sharp needle-shaped protrusions, which run the risk of getting broken off during installation of the fixture. Therefore, according to at least one example embodiment, the fixture surface has not been coated with hydoxylapatite (HA). As regards TPS surfaces, they present pores which are not only difficult for the microorganism-resisting control system (e.g. macrophages) of the human body to access, but are also difficult for a dentist to clean properly. Bad long term results for TPS surface (provided on IMZ implants—now taken off the market) have been acknowledged by Haas, R. et al: *Survival of* 1,920 *IMZ Implants Followed for up to* 100 *Months. The International Journal of Oral & Maxillofacial Implants* 1996; 11:581-588. Therefore, according to at least one example embodiment, the fixture surface has not been coated by titanium plasma spraying (TPS).

As previously mentioned, the inventor has realized that compression of the bone in a direction perpendicularly to the implant surface may result in the formation of small gaps between the bone plugs and the pit walls; the smaller the angles the larger the gaps. It has further been realized that by having pit walls and/or protrusion walls with a substantially constant inclination, i.e. lying in a plane inclined relative to an average plane, the size of the gaps may be kept quite small. In contrast to a substantially uncurved wall, a curved wall may have fewer points of contact with bone subjected to compressive force, and may therefore reduced fixture/bone interface shear strength. Therefore, according to at least one example embodiment, the surface roughness comprises pits and/or protrusions which are defined by walls extending into or from a fixture surface, wherein at least 50% of said pits and/or protrusions have walls having a substantially constant inclination or only a slight curvature with respect to said fixture surface. Said fixture surface may be regarded as a local average area with pits and/or protrusions. Thus, said fixture surface may, for instance, be a flank of a thread or a flat area between two neighbouring thread peaks, etc. Alternatively, at least 50% of the walls defining a pit and/or protrusion are configured with a constant inclination or only a slight curvature with respect to said fixture surface. In this connection, a wall having a radius greater than 10 μm is regarded as a slight curvature.

Furthermore, it has been realized that to keep the potential gaps small, the angle of inclination of the walls should suitably be kept within a common interval. If some walls have very steep inclination while others have a slight inclination, there is a risk that the latter will have unnecessarily large gaps. Therefore, according to at least one example embodiment, the surface roughness comprises pits and/or protrusions which are defined by walls extending into or from a fixture surface, wherein at least 50% of said pits and/or protrusions have walls having an angle of inclination of 30° or more, such as an angle of inclination of 60°±10°, suitably 55°±5°. Other intervals are, however, also conceivable, e.g. 40°±10°, 55°±10°, 60°±5°, 65°±10° or 70°±5°. Furthermore, it may be advantageous to have a larger number of pits and/or protrusions having said angles/intervals, e.g. 55%-95% of said pits and/or protrusions, such as 60%-90%, for instance 65%-85%. Since a pit and/or protrusion may be constituted by several walls, of which not all are within the stated intervals, as an alternative example embodiment, at least 50% of the walls defining pits and/or protrusions have an angle of inclination as stated above, suitably 55%-95% of the walls, such as 60%-90%, for instance 65%-85%.

BRIEF DESCRIPTION OF THE DRAWINGS

FIG. 1a illustrates schematically a dental fixture for insertion into a human jawbone.

FIG. 1b is a schematic magnification of the surface roughness of the fixture in FIG. 1a.

FIG. 1c is a schematic magnification of a nanostructure applied to the surface roughness shown in FIG. 1b.

FIG. 1d is a cross-sectional view of the schematic magnification of the surface roughness shown in FIG. 1b taken across A-A.

FIG. 6a illustrates schematically a dental fixture having an alternative surface roughness compared with the surface roughness shown in FIG. 1b.

FIG. 6b is a schematic magnification of the surface roughness of the fixture in FIG. 6a.

FIG. 6c is a schematic magnification of a nanostructure applied to the surface roughness shown in FIG. 6b.

FIG. 6d is a cross-sectional view of the schematic magnification of the surface roughness shown in FIG. 6b taken across B-B.

DETAILED DESCRIPTION OF THE DRAWINGS

Figure 1:
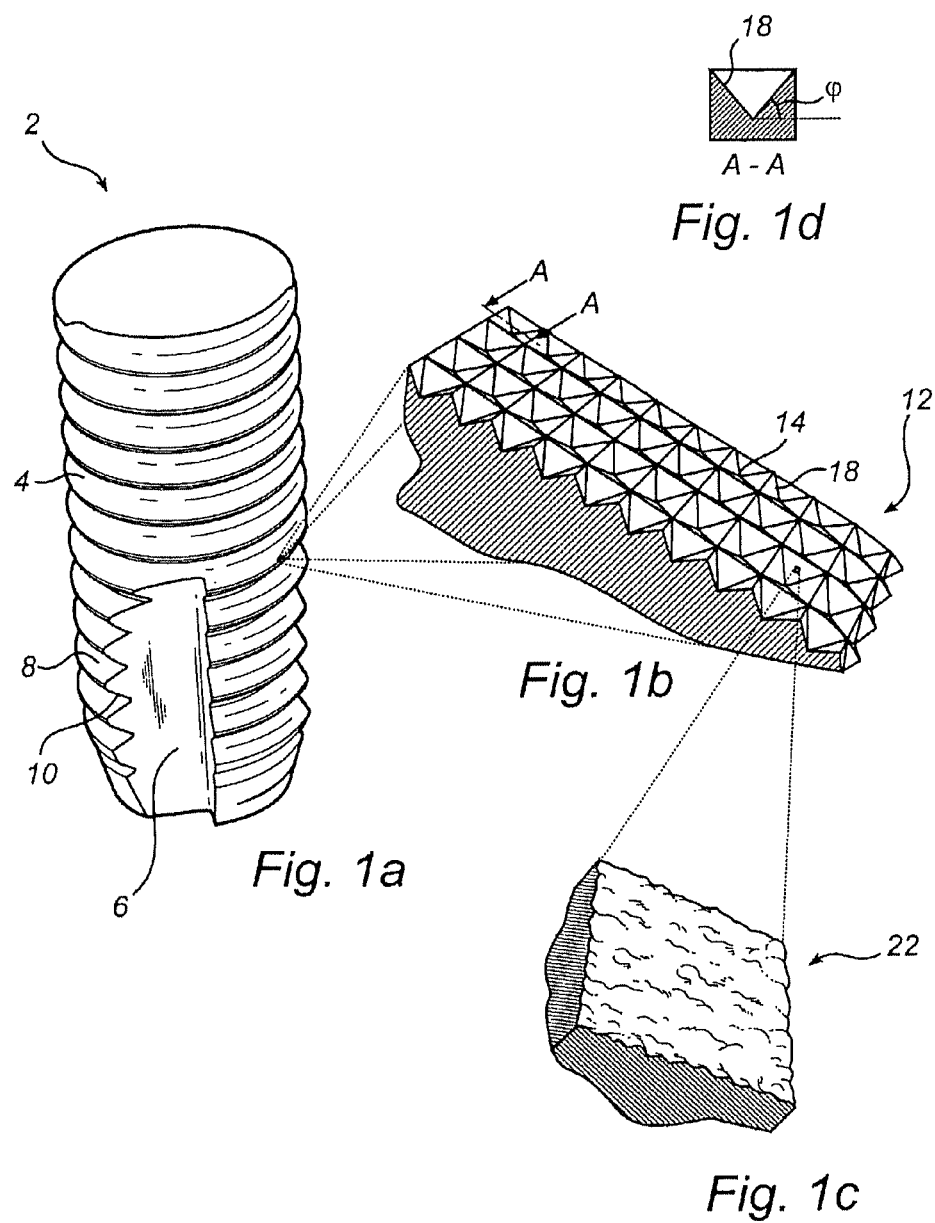

FIG. 1a illustrates schematically a dental fixture 2 for insertion into a human jawbone. The fixture 2 is provided with threads 4 and a cutting recess 6 for self-tapping installation into the bone. The threads 4 have a coronal flank 8 and an apical flank 10. The threads 4 may either be microthreads having a depth of 0.02 mm-0.2 mm, or macrothreads having a depth greater than 0.2 mm, or a combination of microthreads and macrothreads. Although possible to limit a desired inventive surface structure to one of said coronal or apical flanks, for the illustrated fixture, it is assumed that both the coronal flanks 8 and the apical flanks 10 of the threads 4 are provided with an inventive surface roughness. Furthermore, as an alternative to threads, the inventive surface roughness may be present on, for example, circular ridges around the fixture.

The surface roughness 12 is schematically illustrated in the magnification represented by FIG. 1b. While the drawings for illustrative purposes depicts an evenly distributed pattern of pits 14, in practice, the distribution may be more uneven. The pits 14 are herein illustrated as having an inverted generally pyramid shape, however, other shapes are possible. The herein chosen triangular-shaped walls 18 of the pits 14 are in this illustration provided at an angle $\phi$ greater than 50°. When measuring across the pits 14 in a direction from one wall to an opposing wall, the path along the side wall interconnecting the two opposing walls will be generally flat, thus resulting in a somewhat reduced mean slope having a lower value than the inclination of each individual wall. With the proposed wall inclination the mean slope would be greater than tan 30°. The depth of the pits is in this example 6 μm, which gives a roughness average parameter $S_a$ about 1.19 μm.

FIG. 1c is a schematic magnification of a nanostructure 22 applied to the surface roughness shown in FIG. 1b. The nanostructure 22 contributes to bone growth. The size of the nanostructure is about 0.1 μm or more (measured as the roughness average parameter $S_a$ using a Gaussian 2 μm high-pass filter).

Thus, the fixture 2 according to the illustrated embodiment has at least three designed levels of roughness. The threads 4 being a roughness on the millimeter-level, the pattern of pits 14 being a roughness 12 on the micrometer-level, and the nanostructure 22 overlying the pits 14 and being a roughness on the nanometer-level. Although the surface roughness 12 has only been illustrated with pits 14, it may as an alternative be provided with protrusions instead, or a combination of pits and protrusions, as long as the claimed values of the mean slope parameter $R_{sl}$ and the roughness average parameter $S_a$ are fulfilled.

Figure 2:
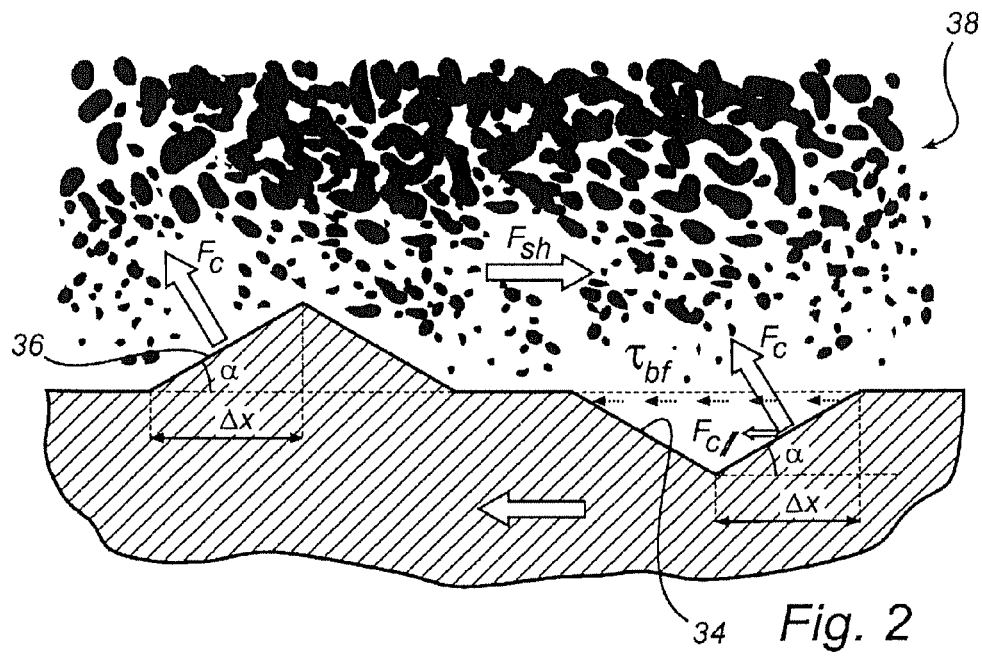
FIG. 2 is a schematic illustration of a surface roughness.

FIG. 2 is a schematic illustration of a surface roughness having pits 34 and protrusions 36. The figure demonstrates how the surface roughness subjects the bone tissue 38 to shear force $F_{sh}$ and compressive force $F_c$. A deeper discussion of the figure has already been presented under the heading "Summary of the Invention".

Figure 3:
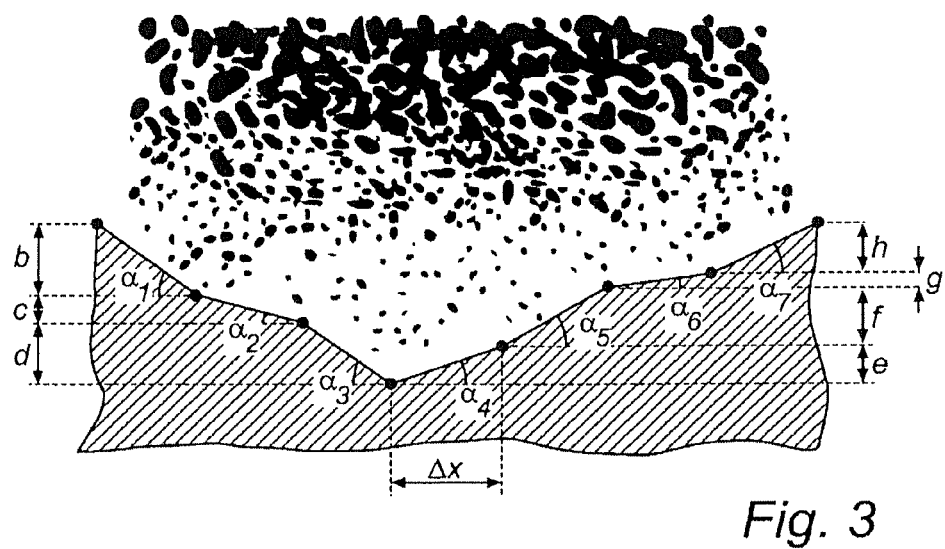
FIG. 3 is a schematic illustration of another surface roughness.

FIG. 3 is a schematic illustration of another surface roughness, or more specifically a surface roughness profile. For simplicity and for exemplifying purpose, in the following calculation it is assumed that no gap is present between the fixture and the bone (i.e. any gap has been neglected). Assuming a width $\Delta y$ and said profile, when the fixture is moved to the right in the figure, the fracture force is obtained by $$F_i = \sigma_{bcf} \Sigma \Delta x \Delta y \tan(\alpha) = \sigma_{bcf} \Sigma \Delta x \Delta y (b/\Delta x + c/\Delta x + d/\Delta x)$$
$$= \sigma_{bcf} \Sigma \Delta y \cdot (b+c+d)$$

When the fixture instead is moved to the left the fracture force becomes:

$$F_i = \sigma_{bcf} \Sigma \Delta x \Delta y \tan(\alpha) = \sigma_{bcf} \Delta y (e+f+g+h)$$

It is obvious that $(b+c+d)=(e+f+g+h)$, which means that the shear strength is equal in both directions. The interface shear strength according to theory of plasticity, $I_{sh}^P$ is $$I_{sh}^P = F_i/(7\Delta x \Delta y) = \sigma_{bcf} \Delta y (b+c+d)/(7\Delta x \Delta y) = \sigma_{bcf}(b+c+d)/(7\Delta x)$$

Since (b+c+d+e+f+g+h)/(7Δx) is the 2D surface roughness parameter mean slope ($R_{sl}$) and since (b+c+d)=(e+f+g+h) the following formula can be set up $$I_{sh}^P = \sigma hd\ bcfR_{sl}/2$$

Thus, when the compressive strength of bone sets the limit for the bone-fixture interface shear strength and when theory of plasticity is applied, the 2D mean slope parameter is an excellent predictor of interface shear strength.

The inventor has come to the conclusion that a mean slope $R_{sl} \geq \tan 30°$, i.e. $R_{sl} \geq 0.577$, is advantageous. With such a mean slope, the bone-fixture interface shear strength becomes $$I_{sh}^P \geq \sigma_{bcf} 0.577/2 = 0.289 \sigma_{bcf}$$

Assuming a compressive strength of 150 MPa the bone-fixture interface shear strength becomes $$I_{sh}^P \geq 43.3\ MPa$$

Such a value of the bone-fixture interface shear strength is indeed satisfactory.

FIGS. 4a-4d and FIGS. 5a-5b are further schematic illustrations of different types of surface roughness profiles.

Figure 4A:
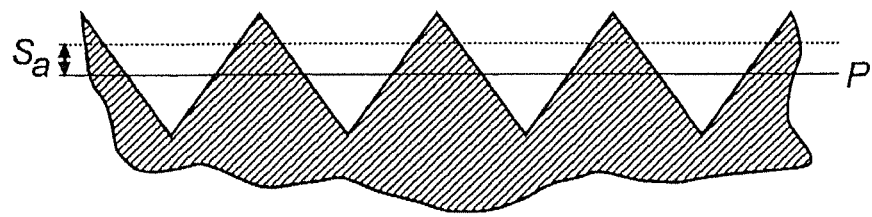
FIG. 4a is a further schematic illustration of a different type of surface roughness profile.
Figure 4B:
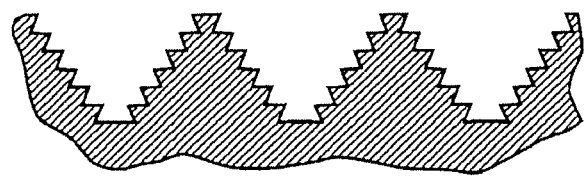
FIG. 4b is a further schematic illustration of another different type of surface roughness profile.
Figure 4C:
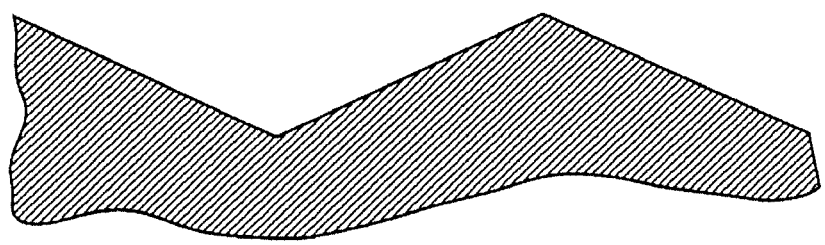
FIG. 4c is a further schematic illustration of another different type of surface roughness profile.
Figure 4D:
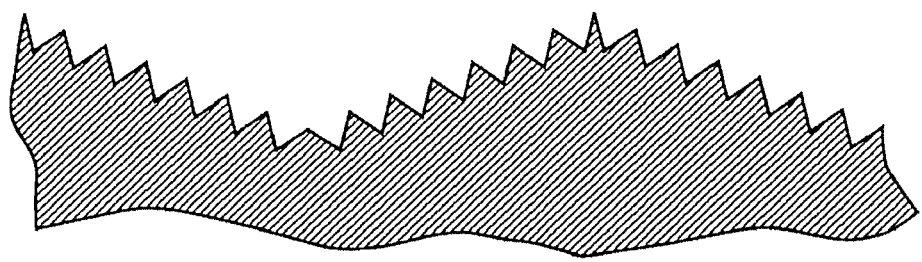
FIG. 4d is a further schematic illustration of another different type of surface roughness profile.

In FIGS. 4a-4d all profiles have substantially the same value of the roughness average parameter $S_a$. As demonstrated in FIG. 4a, the contour of the surface roughness has flanked tops and bottoms. A plane P is indicated in the figure and it represents the average distance from the core to the contour of the surface roughness. The roughness average parameter $S_a$ is the average distance from the contour of the roughened surface to said indicated plane P. In FIGS. 4a-4d, $S_a$ is assumed to be 1 μm or greater. While the roughness average parameter $S_a$ has a satisfactory value in all of the four profiles, only the profiles of FIGS. 4a and 4b have a means slope parameter $R_{sl}$ which is adequate (tan 30° or greater). As can be seen by the naked eye, the mean slope in the profiles of FIGS. 4c and 4d is clearly much lower than in the previous profiles. Thus, if choosing (from these four profiles) a profile for a surface roughness for a fixture, the inventor has come to the conclusion that the profiles in FIGS. 4a and 4b should be chosen rather than the profiles in FIGS. 4c and 4d.

It should be noted that measuring the mean slope and the roughness average parameter of a surface roughness at the micrometer-level requires appropriate filtering, because otherwise the large waviness or small nanostructures would cause miscalculations. Therefore, as previously mentioned, a Gaussian 50 μm high-pass filter and at least a 3 μm (or 4 μm or 5 μm) low pass filter is applied to an original unfiltered set of data representing the surface topography obtained at 50 times magnification by white light interferometry. Although the inventor realizes that the surface may be characterized by other measuring methods, the present one has been found convenient and accurate.

Figure 5A:
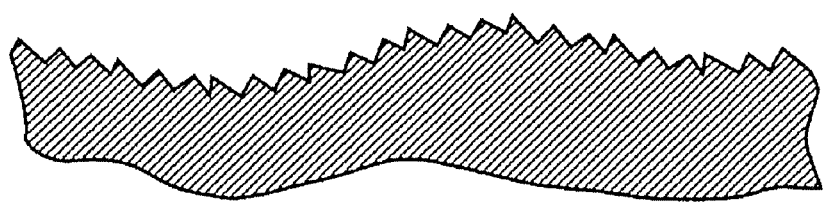
FIG. 5a is a further schematic illustration of another different type of surface roughness profile.
Figure 5B:
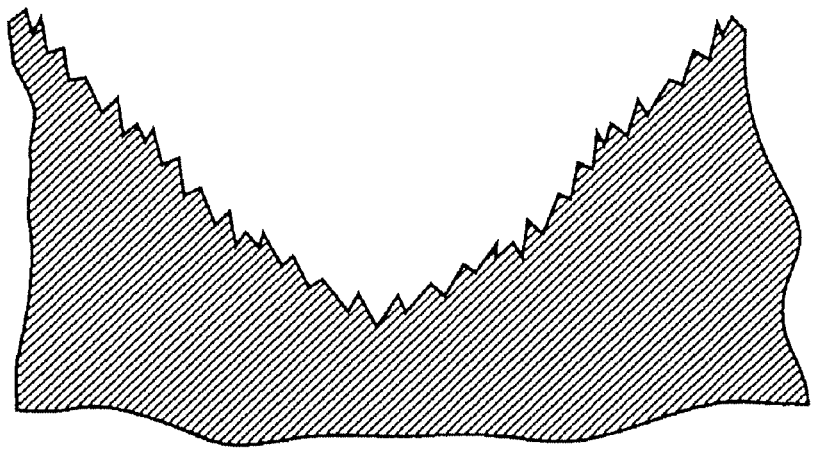
FIG. 5b is a further schematic illustration of another different type of surface roughness profile.

In FIGS. 5a and 5b two surface roughness profiles are compared. The profile of FIG. 5a has a too small mean slope $R_{sl}$ and also too small roughness average parameter $S_a$. In contrast, FIG. 5b has a larger mean slope $R_{sl}$ and a larger roughness average parameter $S_a$. Thus, to increase the interface shear strength without risking reduced fixture/bone contact, the roughness profile in FIG. 5b should be chosen rather than the profile in FIG. 5a.

Figures 6A, 6B, 6C, 6D:
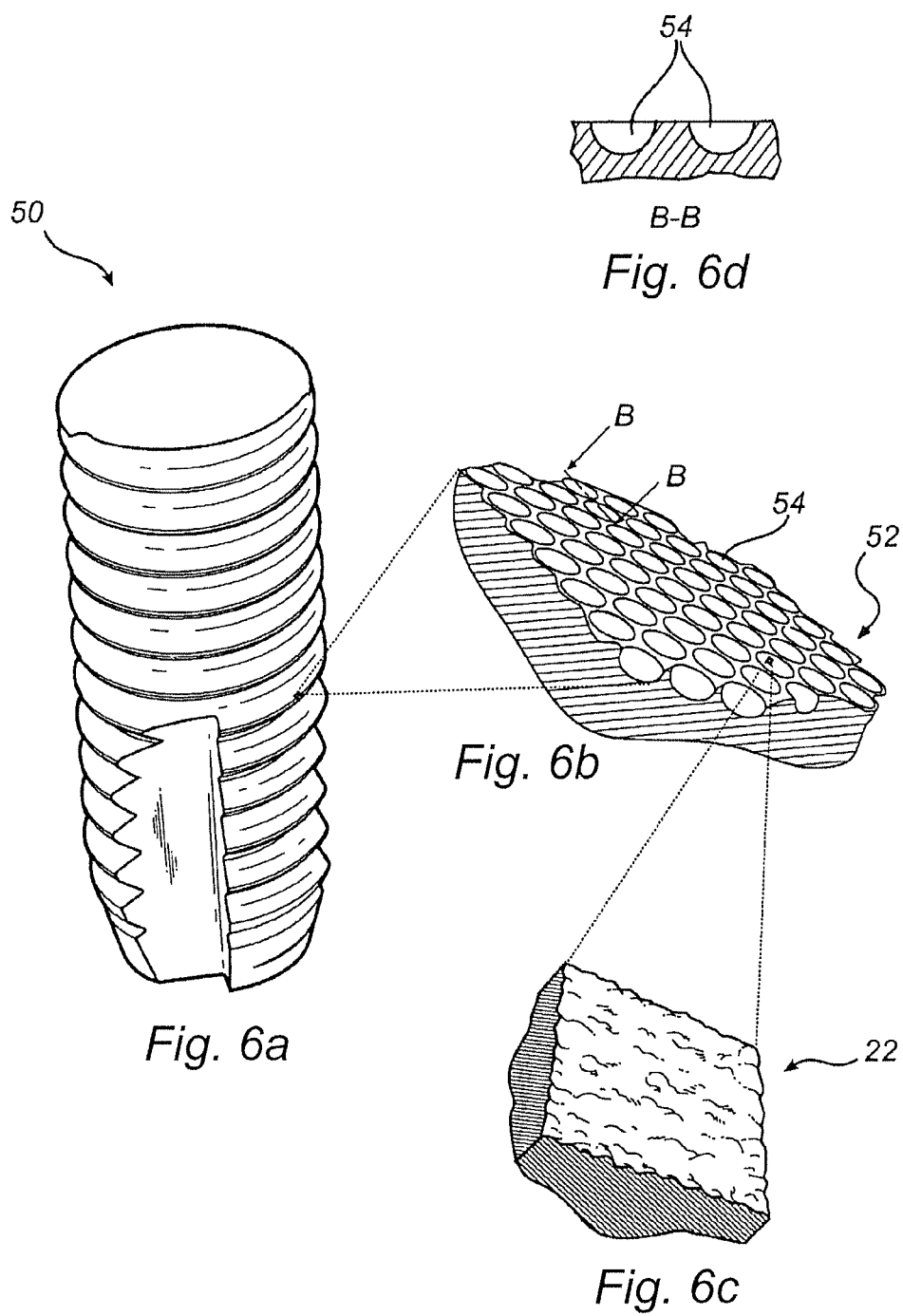

FIG. 6 illustrates schematically a dental fixture 50 having an alternative surface roughness 52 compared with the surface roughness 12 shown in FIG. 1b. In FIG. 6 the surface roughness 52 comprises a pattern of hemispherical pits 54. As shown with the imaginary lines in the detailed top view in FIG. 7, the hemispherical pits 54 are arranged in a honeycomb pattern composed of hexagons. Thus, each hemispherical pit 54 has six neighbouring pits. As further depicted in FIG. 7, the pits 54 have a radius R and the distance from the centre of the pit opening to one side of the corresponding surrounding hexagon is defined as kR, wherein k is a constant. Table 1 shows how the mean slope $R_{sl}$ and the roughness average parameter $S_a$ of a pattern of hemispherical pits 54 vary with different values of R and k.

TABLE 1

Mean slope and roughness average parameter of hemispherical pits depending on pit radius and distance between pits.

| R | K | $S_a$ | $R_{sl}$ | Satisfactory roughness |
|---|---|---|---|---|
| 2 μm | 2.00 | 0.4686 μm | tan 12.8° | No |
| 3 μm | 1.15 | 0.9930 μm | tan 34.4° | No |
| 3 μm | 1.20 | 1.026 μm | tan 32.2° | Yes |
| 3 μm | 1.25 | 1.041 μm | tan 30.1° | Yes |
| 3 μm | 1.30 | 1.044 μm | tan 28.2° | No |
| 4 μm | 1.05 | 1.140 μm | tan 39.4° | Yes |
| 4 μm | 1.25 | 1.389 μm | tan 30.1° | Yes |
| 4 μm | 1.30 | 1.392 μm | tan 28.2° | No |
| 5 μm | 1.00 | 1.231 μm | tan 42.2° | Yes |
| 5 μm | 1.25 | 1.736 μm | tan 30.1° | Yes |
| 10 μm | 1.10 | 3.127 μm | tan 36.9° | Yes |

Figure 7:
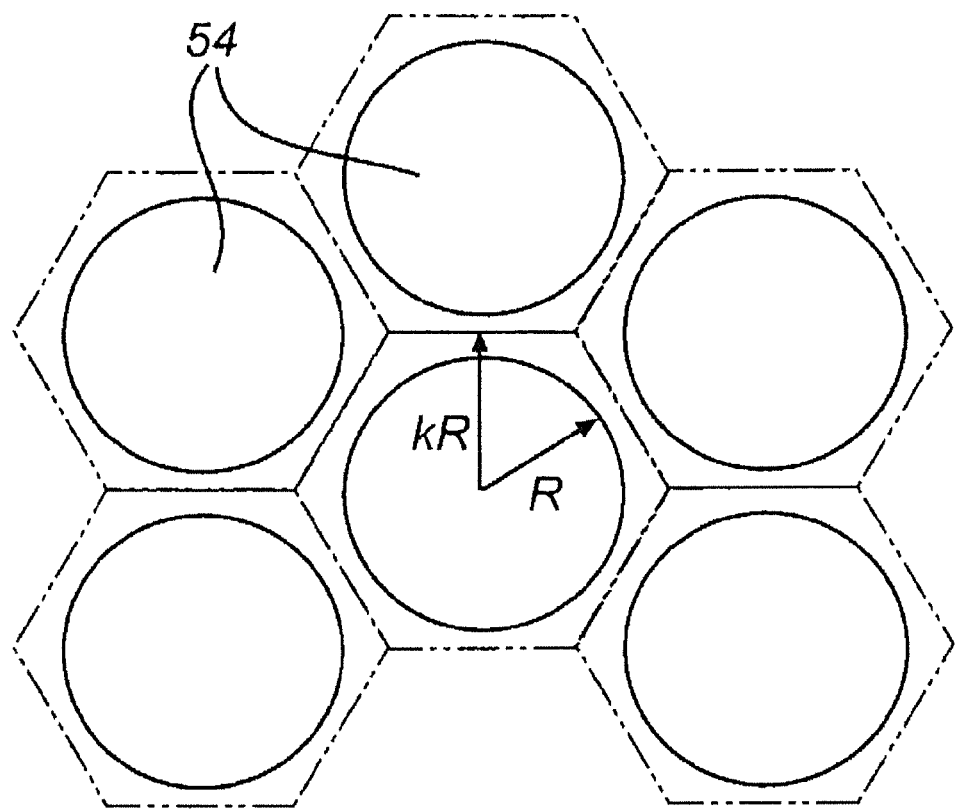
FIG. 7 is a detailed top view of a portion of the surface roughness shown in FIGS. 6a-6d. An imaginary honeycomb pattern has been added for illustrative purposes.

As can be seen in Table 1, for a the pattern of pits 54 shown in FIGS. 6 and 7, the mean slope $R_{sl}$ is dependent on the constant k. For values of k between 1.00 to 1.25 the means slope is more than tan 30°, which is a satisfactory value of the mean slope. However, for k=1.30, the mean slope is tan 28.2°, i.e. too small. The roughness average parameter $S_a$ increases with increased radius R. Even with a relatively high value of k=2.00, the $S_a$ value is not high enough when the radius R=2 μm. On the other hand, when R=3 μm, the constant k can be as low as 1.20 to obtain a satisfactory $S_a$ greater than 1 μm. With a radius as large as 10 μm, k can be as low as 1.10 and still pass the acceptable limit for the roughness average parameter $S_a$.

It should be understood that those combined values of R and k in Table 1 which do not provide a satisfactory roughness for the pattern of hemispherical pits 54, would do so if the pits were made deeper, e.g. making pits in the form of hemiellipsoids instead of hemispheres. Deeper pits would increase both the mean slope $R_{sl}$ and the roughness average parameter $S_a$. Thus, similarly to the roughness in FIG. 1b, the roughness in FIGS. 6 and 7 is merely shown as a non-limiting example.

Similarly to the embodiment illustrated in FIGS. 1a-1c, a nanostructure 22 may be applied to the surface roughness of the embodiment shown in FIG. 6.

The hemispherical pits 54 in FIGS. 6 and 7 may suitably be provided by any one of the previously mentioned methods. For instance, FIGS. 8a-8b shows the production of the surface roughness in FIGS. 6 and 7 by means of laser ablation.

Figure 8A:
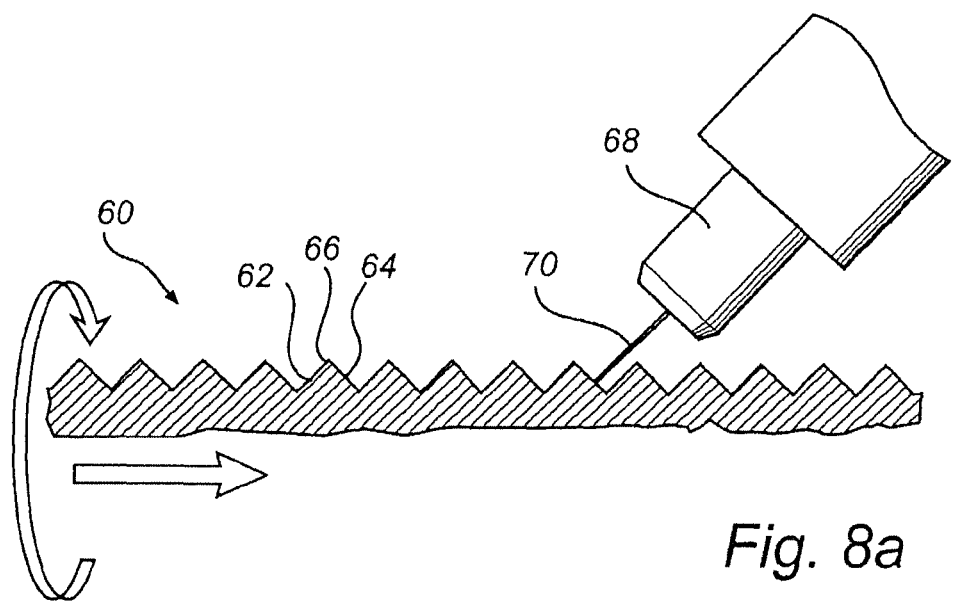
FIG. 8a illustrates an aspect of a method of producing the surface roughness shown in FIGS. 6a-d and 7.
Figure 8B:
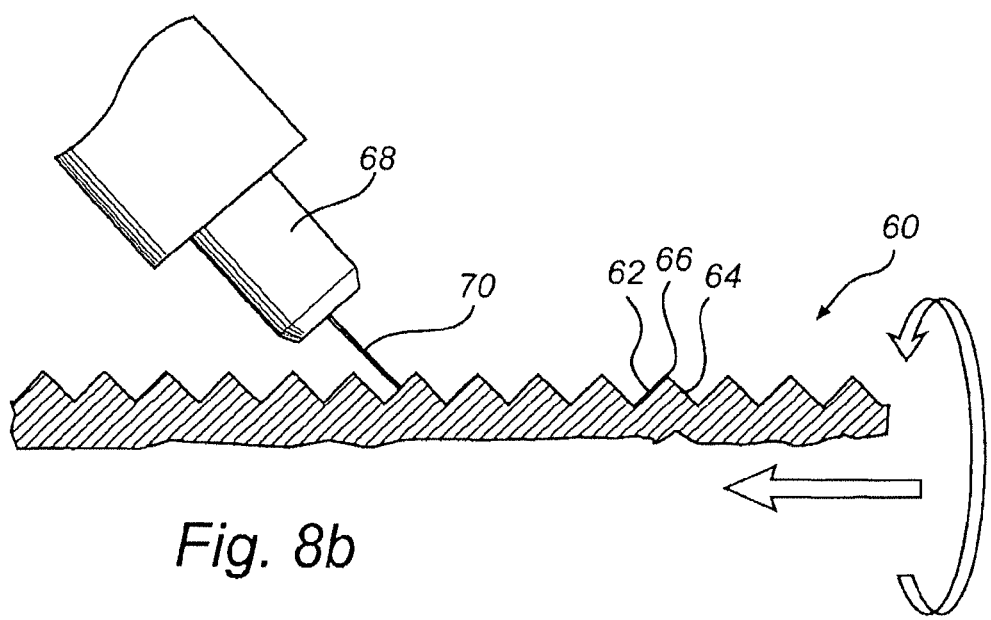
FIG. 8b illustrates another aspect of a method of producing the surface roughness shown in FIGS. 6a-d and 7.

FIG. 8a schematically shows the thread profiles 60 of the fixture. A thread profile has a coronal flank 62 and an apical flank 64 and an apex 66 formed by the intersection of said two flanks 62, 64. As schematically illustrated, the fixture is moved in the apical direction and rotated relative to a laser 68 that emits laser pulses 70 to the fixture surface to produce the pits on the apical flanks 64. In FIG. 8b, the fixture is moved in the coronal direction and rotated in order to produce pits on the coronal flanks 62. To avoid redeposition of the ablated material back onto the target surface, the ablated vapours may be sucked away by a suitable suction device.

The invention claimed is:
1. A dental fixture for insertion into a human jawbone, comprising a bone contacting surface, wherein at least 50% of the bone-contacting surface is designed such that when a Gaussian 50 μm high-pass filter and a Gaussian 3 μm low-pass filter is applied to an original unfiltered set of measurement data which represents a topography of said surface and which is obtained at 50 times magnification by white light interferometry, the resulting filtered set of data presents a surface topography of the implant, the implant having a surface roughness having a value of the roughness average parameter $S_a \geq 1$ μm and having a value of the two-dimensional mean slope parameter ranging from $R_{sl} \geq \tan 30°$ to $R_{sl} \leq \tan 70°$, wherein the surface roughness of the implant comprises pits and/or protrusions which are defined by walls extending into or from a fixture surface, wherein at least 50% of said pits and/or protrusions have walls having an angle of inclination of 30° or more.

2. The dental fixture as claimed in claim 1, wherein said bone contacting surface has a coronal end and an apical end, wherein said surface roughness is present at least at an area located closer to the coronal end than to the apical end, suitably at least at an area located within the first third of the total axial extent from the coronal end to the apical end.

3. The dental fixture as claimed in claim 1, wherein when a Gaussian 4 μm low-pass filter is applied instead of said 3 μm low-pass filter, the resulting filtered image presents said surface topography, the implant having a surface roughness having a value of the roughness average parameter $S_a \geq 1$ μm and having a value of the two-dimensional mean slope parameter $R_{sl} \geq \tan 30°$ to $R_{sl} \leq \tan 70°$.

4. The dental fixture as claimed in claim 1, wherein when a Gaussian 5 μm low-pass filter is applied instead of said 3 μm low-pass filter, the resulting filtered image presents said surface topography, the implant having a surface roughness having a value of the roughness average parameter $S_a \geq 1$ μm and having a value of the two-dimensional mean slope parameter $R_{sl} \geq \tan 30°$ to $R_{sl} \leq \tan 70°$.

5. The dental fixture as claimed in claim 1, wherein the two-dimensional mean slope parameter $R_{sl} \geq \tan 35°$ to $R_{sl} \leq \tan 70°$.

6. The dental fixture as claimed in claim 1, wherein the roughness average parameter $S_a \geq 1.5$ μm.

7. The dental fixture as claimed in claim 1, comprising a thread for inserting the fixture into the jawbone by means of rotation, wherein the thread is provided with said surface roughness.

8. The dental fixture as claimed in claim 7, wherein the thread has a thread profile comprising two flanks and an apex formed by the intersection of said two flanks, wherein both flanks are provided with said surface roughness.

9. The dental fixture as claimed in claim 1, wherein said pits and grooves forming said surface roughness are is superposed by a nanostructure which has a value of the roughness average parameter $S_a \geq 0.1$ μm when measured by applying a Gaussian 2 μm high-pass filter to said set of measurement data.

10. The dental fixture as claimed in claim 1, wherein said surface roughness is produced by anyone of or any combination of the methods selected from the group consisting of:
knurling the surface of the fixture,
etching,
blasting,
nanolithography, and
laser ablation.

11. The dental fixture as claimed in claim 1, wherein the fixture surface is at least partly presented by a machined titanium surface.

12. The dental fixture as claimed in claim 1, with the proviso that the fixture surface has not been coated with hydoxylapatite (HA).

13. The dental fixture as claimed in claim 1, with the proviso that the fixture surface has not been coated by titanium plasma spraying (TPS).

14. The dental fixture as claimed in claim 1, wherein at least 50% of said walls of said pits and/or protrusions forming the surface roughness of the implant have a substantially constant inclination.

15. The dental fixture as claimed in claim 1, wherein the two-dimensional mean slope parameter ranges from $R_{sl} \geq \tan 40°$ to $R_{sl} \leq \tan 70°$.

16. The dental fixture as claimed in claim 1, wherein the roughness average parameter $S_a \geq 2$ μm.

17. The dental fixture as claimed in claim 1, wherein at least 50% of said walls of said pits and/or protrusions have an angle of inclination of 60°±5.

18. The dental fixture as claimed in claim 1, wherein at least a percentage of said walls of said pits and/or protrusions forming the surface roughness have only a slight curvature with respect to said fixture surface.

\* \* \* \* \*